Figure 1:
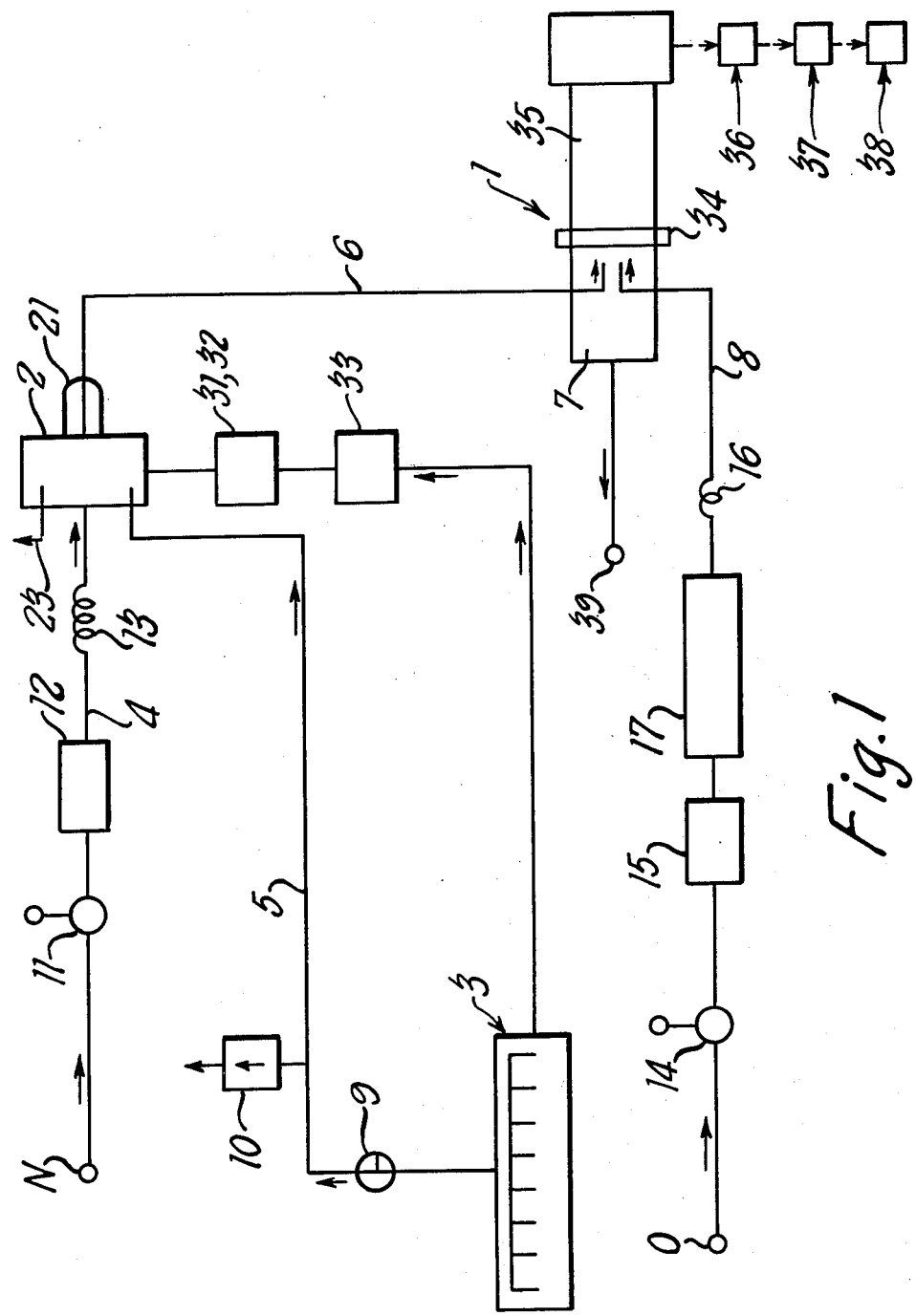

United States Patent [19]

Dymond et al.

[11] 4,257,777
[45] Mar. 24, 1981

[54] GAS DETECTION

[75] Inventors: Harry F. D. Dymond, Southampton; Albert E. Yallup, Totton, both of England

[73] Assignee: British-American Tobacco Company Limited, London, England

[21] Appl. No.: 59,372

[22] Filed: Jul. 20, 1979

Related U.S. Application Data

[63] Continuation of Ser. No. 891,500, Mar. 30, 1978, abandoned.

[30] Foreign Application Priority Data

Apr. 12, 1977 [GB] United Kingdom ............... 15131/77

[51] Int. Cl.³ .......................................... G01N 21/76
[52] U.S. Cl. .................................... 23/232 E; 23/927; 422/52
[58] Field of Search ................. 73/23; 23/232 E, 927; 422/52, 93

[56] References Cited

U.S. PATENT DOCUMENTS

| | | | |
|---|---|---|---|
| 3,520,660 | 7/1970 | Webb | 422/52 X |
| 3,528,435 | 9/1970 | Morrissey | 73/23 X |
| 3,586,007 | 6/1971 | Kelley et al. | 73/23 X |
| 3,647,387 | 3/1972 | Benson et al. | 422/52 |
| 3,996,002 | 12/1976 | Fine | 23/232 E X |
| 3,996,003 | 12/1976 | Fine et al. | 23/230 PC |
| 4,049,383 | 9/1977 | Burton et al. | 422/52 |
| 4,113,434 | 9/1978 | Tanaka et al. | 422/93 X |

*Primary Examiner*—Michael Marcus
*Attorney, Agent, or Firm*—Kane, Dalsimer, Kane, Sullivan & Kurucz

[57] ABSTRACT

The invention comprises a method and apparatus for the detection, or detection and concentration determination, of nitric oxide in a gas mixture, particularly in tobacco smoke. The apparatus comprises sampling means operable to isolate a predetermined amount of the gas mixture and pass it to a reaction chamber, means for supplying to that chamber a further gas chemiluminescently reactable with the nitric oxide, and detection means responsive to luminescence emitted in the said chamber. The method comprises operating sampling means to isolate a predetermined amount of the gas mixture and supply it to a reaction chamber, supplying to that chamber a further gas chemiluminescently reactable with the nitric oxide, and operating means to detect luminescence in the said chamber. A carrier gas may be used for transferring the predetermined amount of gas mixture from the sampling means to the reaction chamber.

5 Claims, 3 Drawing Figures

GAS DETECTION

This is a continuation of application Ser. No. 891,500, filed Mar. 30, 1978, now abandoned.

This invention relates to gas detection, particularly the detection of nitric oxide at low concentration in a gaseous mixture. It has special relevance to the detection or concentration measurement of nitric oxide in tobacco smoke.

The invention provides an improved method and apparatus for the detection of nitric oxide at low concentration in a mixture of gases by detecting luminescence emitted in a chemiluminescent reaction between nitric oxide gas and a further gas.

According to this invention, apparatus for the detection or detection and concentration determination of nitric oxide in a gas mixture comprises a reaction chamber, sampling means operable to isolate a predetermined amount of the gas mixture and to pass the same to the reaction chamber, means for supplying to that chamber a further gas chemiluminescently reactable with the nitric oxide, and detection means disposed to respond to luminescence emitted in said chamber.

Advantageously, the apparatus comprises also means for supplying a carrier gas to the sampling means, which is operable to permit the isolated volume of the gas mixture to be swept by the carrier gas to the reaction chamber. Preferably the apparatus includes timing means operable in response to signals from a source of the gas mixture, a cigarette-smoking machine for example, to activate the sampling means. Thus, if the apparatus includes a smoking machine, the sampling means may be operated so as to take, at a predetermined time in the cycle of the machine, a sample of smoke from a flow emanating therefrom.

Also according to the invention, a method for the detection or detection and concentration determination of nitric oxide in a gas mixture comprises operating sampling means to isolate a predetermined amount of the gas mixture, supplying the said amount of the mixture to a reaction chamber, supplying to that chamber a further gas chemiluminescently reactable with the nitric oxide, and operating chemiluminescence-detecting means to detect luminescence in the said chamber.

Figure 2:
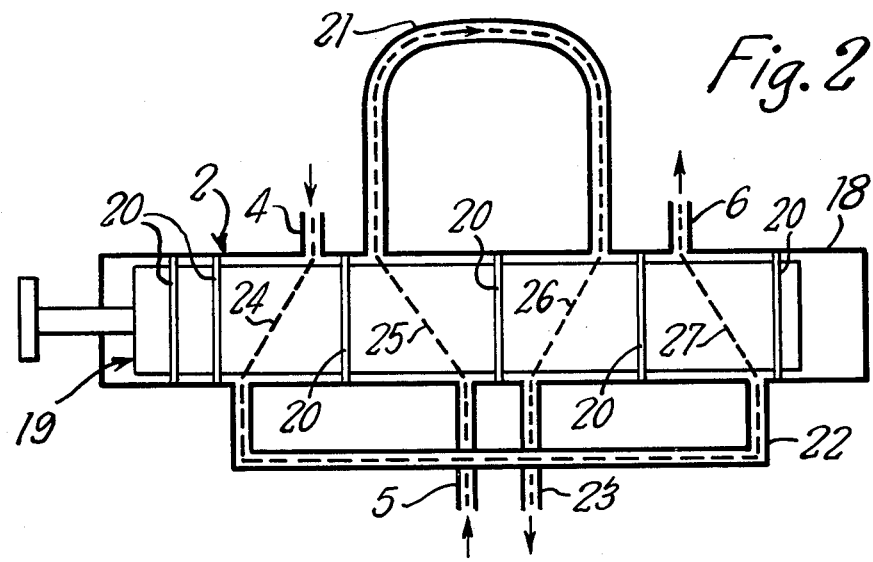

One manner of carrying the invention into effect will now be more fully described, by way of example, with reference to the accompanying diagrammatic drawings, in which:

FIG. 1 is a diagram of apparatus for detecting nitric oxide in cigarette smoke,

FIG. 2 a section to a larger scale through a sampling valve, and

Figure 3:
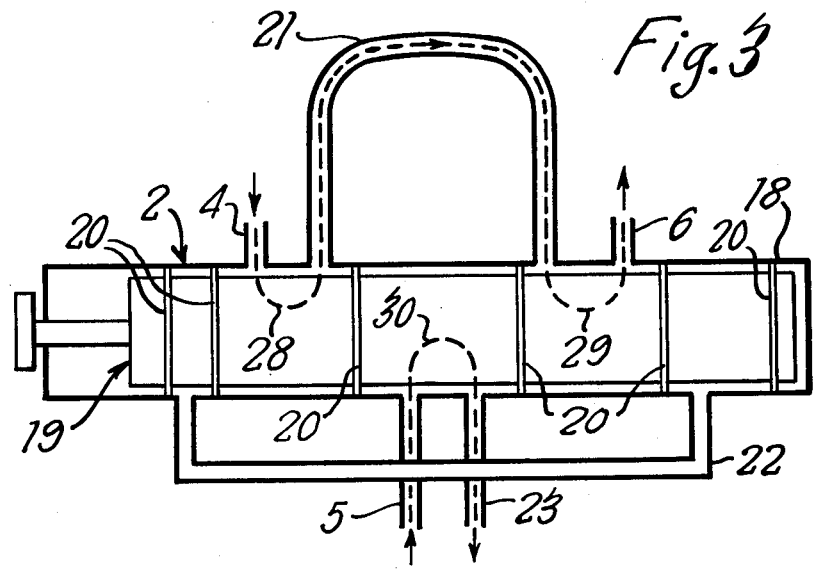

FIG. 3 the same section, but indicating a different operative condition of the valve.

Referring to FIG. 1, the apparatus comprises a detector unit 1, a sampling valve 2 and a cigarette-smoking machine 3 as source of gas mixture. A line 4 supplies nitrogen, to serve as inert carrier gas, from a source N thereof to the sampling valve 2. A line 5 serves to convey cigarette smoke to the valve 2 from the machine 3. A line 6 is provided for the passage of cigarette smoke and carrier gas from the valve 2 to a reaction chamber 7 of the unit 1. A line 8 is provided for the supply of partially ozonized oxygen from a source O to the chamber 7.

The machine 3, for example that marketed by Cigarette Components Ltd. under the model designation 302, has eight smoking stations. In the smoking phase of its cycle of operation, smoke is supplied simultaneously by way of a manifold from all eight of the stations to the line 5, which includes a three-way valve 9 by which standard gaseous mixtures can be introduced into the line for the purpose of calibrating the apparatus. Downstream of the valve 9, there is a pressure-release valve 10 which is used to divide the stream of smoke from the machine. The exhaust from the valve 10, i.e. that part of the smoke which does not pass on through the line 5, may be collected for the determination of the concentration of gases other than nitric oxide, for example carbon monoxide. The nitrogen line 4 includes a variable-pressure controller 11, a variable-flow controller 12 and a restrictor 13. The oxygen line 8 similarly includes a variable-pressure controller 14, a variable-flow controller 15 and a restrictor 16. The line 8 also includes, between the controller 15 and restrictor 16, an electrical-discharge ozonizer 17. The pressure controllers 11 and 14 are each provided with a pressure gauge and the flow controllers 12 and 15 with a Vernier dial, for fine adjustment of the nitrogen and oxygen flow rates respectively.

Referring to FIGS. 2 and 3, the sampling valve 2 comprises a cylindrical casing 18 within which there is slidably received a valve spool 19 on which a number of 'O'-ring seals 20 are fitted. The valve 2 further comprises a sampling loop 21, whose internal volume is exactly 1 cm$^3$, and a bypass loop 22. The lines 4, 5 and 6 are connected to the casing 18 as shown, as is also a venting line 23. Depending upon the position of the valve spool 19, a number of transfer passages are formed between the said spool and the casing 18 by the seals 20, as indicated at 24–27 (FIG. 2) and 28–30 (FIG. 3). The spool is movable from a withdrawn position shown in FIG. 2 to the position shown in FIG. 3 and is returnable to the position of FIG. 2 by solenoids 31 and 32 respectively (FIG. 1). The solenoids 31 and 32 are energised under the control of a timing unit 33 operable in response to signal pulses generated at the smoking machine 3.

In the condition of the valve (FIG. 2), in which the spool 19 is withdrawn to the left-hand side, continuously supplied nitrogen flows into the valve from the line 4 and then, via spool passage 24, by pass loop 22 and spool passage 27, to the line 6, through which it flows to the reaction chamber 7, which it serves to scavenge at this stage. Smoke delivered from the line 5 is directed via the spool passage 25 to the sampling loop 21 and thence via spool passage 26 to the venting line 23. Upon reception of a signal pulse form the machine 3, the timing unit 33 causes the solenoid 31 to move the valve spool 19 to the sample-delivery position shown in FIG. 3. In this condition of the valve 2, nitrogen from the line 4 passes through spool passage 28 and sweeps a representative sample, of predetermined volume, of smoke present in the loop 21 via spool passage 29 to the line 6 for delivery to the reaction chamber 7. The supply of smoke from the line 5 is diverted via spool passage 30 to venting line 23.

Referring to FIG. 1, the detector unit 1 has a red-light filter 34 towards which the ends of the sample line 6 and ozone line 8 are directed and, on the side of the filter remote from the reaction chamber 7, a photomultiplier tube 35 having an extended "S20" cathode. The filter 34 is selected to permit some red and some near infra red light to pass to the tube 35. The electronic output from the latter is fed by way of an amplifier 36 to a push-button attenuator 37, whose output can be fed in turn to a strip-chart recorder 38 for visual representation of nitric-oxide concentration detected in the smoke sample. At the end remote from the filter 34, the chamber 7 has an exhaust connection 39.

Suitably, for operation of the apparatus, the flow rate and pressure of the nitrogen supply are set to 150 cm$^3$ min$^{-1}$ and $1.4 \times 10^5$Nm$^{-2}$ respectively. For the oxygen supply, the flow rate is set to 30 cm$^3$ min$^{-1}$ and the pressure to $1.4 \times 10^4$Nm$^{-2}$. When the sampling valve 2, initially in its withdrawn condition (FIG. 2), is moved to its sample-delivery condition (FIG. 3), a smoke sample is swept by the nitrogen into the reaction chamber 7. At the same time, a proportion of oxygen ozonized in the ozonizer 17 is delivered via the line 8 to the chamber 7 and chemiluminescent reaction between the ozone and nitric oxide in the smoke sample is detected and quantified by the photomultiplier tube 35. The nitric-oxide concentration is indicated by the recorder 38.

The above-described apparatus can be operated, if required, for puff-by-puff analysis of cigarette smoke. The detection of nitric oxide takes place very quickly after the initial production of the smoke. The apparatus is capable of detecting and measuring concentrations of nitric oxide up to about 5,000 VPM (parts per million by volume).

The sampling valve 2 could, instead of being automatically activated, be manually operated. Also other sampling means for isolating a predetermined volume of gaseous mixture could be employed.

We claim:

1. Apparatus for the detection of nitric oxide in a gas mixture, comprising; a reaction chamber, sampling means operable to isolate a predetermined amount of the gas mixture, means for supplying a carrier gas to the sampling means, which is further operable to permit the isolated amount of the gas mixture to be swept by the carrier gas as part of a continuous flow into and out of the reaction chamber, the sampling means including a sampling valve having a sampling passage and a bypass passage, the valve including sealing means which in a first position of the valve isolates the sampling passage while the carrier gas is continuously flowing through the bypass passage and preventing intermixing between the carrier gas and gas in the sampling passage and the valve being shiftable to a second position to direct the carrier gas to pass through the sampling passage and sweep the contents thereof as an isolated amount of gas mixture into and out of the reaction chamber, timing means for shifting the valve between the first and second positions at desired intervals of time, means for supplying to the reaction chamber a further gas chemiluminescently reactable with the nitric oxide, and detection means disposed to respond to luminescence emitted in the chamber.

2. The invention in accordance with claim 1 wherein the means for supplying the gas mixture includes a cigarette-smoking machine and the timing means is operable in response to signals from the machine to activate the sampling means.

3. The invention in accordance with claim 1 wherein the detection means comprises means for determining the concentration of the nitric oxide.

4. A method for the detection of nitric oxide in a gas mixture, which comprises: withdrawing from a source thereof a gas mixture suspected of containing nitric oxide, continuously passing an inert carried gas to and through a sampling valve and a reaction chamber, shifting said sampling valve to a first position, passing said gas mixture to said valve and passing said carrier gas through a by-pass passage in said valve during the maintenance of said valve in said first position without any intermixing between said carrier gas and said gas mixture, shifting said valve to a second position to seal and isolate a sample of a predetermined amount of said gas mixture thereto and to divert said by-passed carrier gas stream to said isolated gas sample, sweeping said isolated sample from said valve as a discrete sample in said continuous flow of said carrier gas into and out of said reaction chamber, supplying ozone to said reaction chamber and reacting said ozone with any nitric oxide present in said gas sample, detecting the presence of nitric oxide by the luminescence produced in the reacting step, and shifting said valve between said first and second positions at predetermined time intervals.

5. The invention in accordance with claim 4, wherein the gas mixture is tobacco smoke which is supplied from a cigarette-smoking machine.

* * * * *